(12) United States Patent
Mault

(10) Patent No.: US 6,620,106 B2
(45) Date of Patent: Sep. 16, 2003

(54) INDIRECT CALORIMETRY SYSTEM

(75) Inventor: James R. Mault, Evergreen, CO (US)

(73) Assignee: Healthetech, Inc., Golden, CO (US)

(*) Notice: Subject to any disclaimer, the term of this patent is extended or adjusted under 35 U.S.C. 154(b) by 0 days.

(21) Appl. No.: 09/968,086

(22) Filed: Oct. 1, 2001

(65) Prior Publication Data
US 2002/0077765 A1 Jun. 20, 2002

Related U.S. Application Data

(60) Provisional application No. 60/236,829, filed on Sep. 29, 2000.

(51) Int. Cl.$^7$ ................................................ A61B 5/08
(52) U.S. Cl. ................ 600/532; 600/538; 600/531; 600/529; 604/65; 604/66
(58) Field of Search ................ 600/529–543, 600/300–301; 604/65–67, 31; 128/204.23

(56) References Cited

U.S. PATENT DOCUMENTS

| | | | |
|---|---|---|---|
| 2,630,798 A | 3/1953 | White et al. | 128/2.07 |
| 2,826,912 A | 3/1958 | Kritz | 73/194 |
| 2,831,348 A | 4/1958 | Kritz | 73/861.28 |
| 2,838,399 A | 6/1958 | Vogel, Jr. | 99/48 |
| 2,869,357 A | 11/1959 | Kritz | 73/32 |
| 2,911,825 A | 11/1959 | Kritz | 73/194 |
| 2,920,012 A | 1/1960 | Sanders et al. | 167/51.5 |
| 3,213,684 A | 10/1965 | Seaton et al. | 73/190 |
| 3,220,255 A | 11/1965 | Scranton et al. | 73/204 |
| 3,250,270 A | 5/1966 | Bloom | 128/2.07 |
| 3,306,283 A | 2/1967 | Arp | 128/2.07 |
| 3,523,529 A | 8/1970 | Kissen | 128/2.07 |
| 3,527,205 A | 9/1970 | Jones | 128/2.08 |
| 3,681,197 A | 8/1972 | Smith | 195/63 |
| 3,726,270 A | 4/1973 | Griffis et al. | 128/2.08 |
| 3,797,480 A | 3/1974 | Williams | 128/2.08 |
| 3,799,149 A | 3/1974 | Rummel et al. | 128/2.07 |
| 3,814,091 A | 6/1974 | Henkin | 128/188 |
| 3,834,375 A | 9/1974 | Sanctuary et al. | 128/2.07 |

(List continued on next page.)

FOREIGN PATENT DOCUMENTS

| | | |
|---|---|---|
| DE | 198 10 476 | 9/1998 |
| EP | 0459647 | 12/1991 |
| EP | 0 712 638 | 12/1995 |
| EP | 1013221 A1 | 6/2000 |
| GB | 2323292 | 9/1998 |
| WO | WO 96/40340 | 12/1996 |
| WO | 99/60925 | 5/1999 |

OTHER PUBLICATIONS

Medical Progress Through Technology, vol. 9, No. 1, 1982 Berlin (D), pp. 27–32, R. Salminen et al., "Computerized Breath–By–Breath Analysis of Respiratory Variables During Exercise".

British Journal Of Anaesthesia, vol. 49, 1977 London (GB) pp. 575–587, J. A. Bushman et al. "Closed Circuit Anaesthesia".

IEEE Transactions On Biomedical Engineering, vol. 35, No. 9, Sep. 1988, pp. 653–659, Capek et al., "Noninvasive Measurement of Cardiac Output Using Partial $CO_2$ ReBreathing".

Clinics In Chest Medicine (Review), vol. 10, 1989, pp. 255–264, Heigenhauser et al., "Measurement of Cardiac Output by Carbon Rebreathing Methods".

Primary Examiner—Robert L. Nasser
Assistant Examiner—Patricia C. Mallari
(74) Attorney, Agent, or Firm—Gifford, Krass, Groh, Sprinkle, Anderson & Citkowski, P.C.

(57) ABSTRACT

An indirect calorimetry system includes transducers sensitive to expired airflow that are enclosed within a calorimeter housing, and a microprocessor in communication with the transducers for calculating expiration characteristics. A graphical display displays the expiration characteristics. A communication link transmits expiration characteristics to external devices such as a computer, communication network, or PDA.

30 Claims, 3 Drawing Sheets

U.S. PATENT DOCUMENTS

| | | |
|---|---|---|
| 3,895,630 A | 7/1975 | Bachman .................... 128/2.07 |
| 3,938,551 A | 2/1976 | Henkin ........................ 137/613 |
| 3,962,917 A | 6/1976 | Terada .......................... 73/204 |
| 4,003,396 A | 1/1977 | Fleischmann ................ 137/83 |
| 4,051,847 A | 10/1977 | Henkin ..................... 128/145.6 |
| 4,078,554 A | 3/1978 | Lemaitre et al. ........... 128/2.08 |
| 4,111,036 A | 9/1978 | Frechette et al. .............. 73/23 |
| 4,186,735 A | 2/1980 | Henneman et al. .... 128/201.25 |
| 4,188,946 A | 2/1980 | Watson et al. ......... 128/204.22 |
| 4,197,857 A | 4/1980 | Osborn ........................ 600/531 |
| 4,200,094 A | 4/1980 | Gedeon et al. ........ 128/201.13 |
| 4,211,239 A | 7/1980 | Raemer et al. ............. 128/716 |
| 4,221,224 A | 9/1980 | Clark .......................... 128/718 |
| 4,230,108 A | 10/1980 | Young |
| 4,341,867 A | 7/1982 | Johansen .................... 435/189 |
| 4,359,057 A | 11/1982 | Manzella .................... 128/718 |
| 4,368,740 A | 1/1983 | Binder ........................ 128/718 |
| 4,386,604 A | 6/1983 | Hershey ..................... 128/718 |
| 4,425,805 A | 1/1984 | Ogura et al. ............. 73/861.29 |
| 4,440,177 A | 4/1984 | Anderson et al. ........... 600/532 |
| 4,444,201 A | 4/1984 | Itoh ............................ 128/716 |
| 4,463,764 A | 8/1984 | Anderson et al. ........... 600/532 |
| 4,551,133 A | 11/1985 | Zegers de Beyl et al. .... 604/66 |
| 4,572,208 A | 2/1986 | Cutler et al. ................ 128/718 |
| 4,598,700 A | 7/1986 | Tamm ........................ 128/671 |
| 4,608,995 A | 9/1986 | Linnarsson et al. ......... 128/713 |
| 4,619,269 A | 10/1986 | Cutler et al. ................ 128/719 |
| 4,637,987 A | 1/1987 | Minten et al. ............... 436/151 |
| 4,648,396 A | 3/1987 | Raemer ...................... 600/534 |
| 4,658,832 A | 4/1987 | Brugnoli ..................... 600/532 |
| 4,753,245 A | 6/1988 | Gedeon ...................... 128/718 |
| 4,756,670 A | 7/1988 | Arai ............................. 417/43 |
| 4,781,184 A | 11/1988 | Fife ....................... 128/205.12 |
| 4,796,639 A | 1/1989 | Snow et al. ................. 600/532 |
| 4,850,371 A | 7/1989 | Broadhurst et al. ......... 600/532 |
| 4,856,531 A | 8/1989 | Merilainen ................. 600/532 |
| 4,909,259 A | 3/1990 | Tehrani ...................... 600/531 |
| 4,914,959 A | 4/1990 | Mylvaganam et al. ... 73/861.28 |
| 4,917,108 A | 4/1990 | Mault ......................... 600/531 |
| 4,955,946 A | 9/1990 | Mount et al. ............... 600/532 |
| 4,966,141 A | 10/1990 | Bacaner et al. ........ 128/207.14 |
| 4,986,268 A | 1/1991 | Tehrani ...................... 128/204 |
| 4,998,018 A | 3/1991 | Kurahashi et al. .......... 250/343 |
| 5,022,406 A | 6/1991 | Tomlinson ................. 128/719 |
| 5,038,773 A | 8/1991 | Norlien et al. ......... 128/205.23 |
| 5,038,792 A | 8/1991 | Mault ......................... 128/718 |
| 5,042,500 A | 8/1991 | Norlien et al. .............. 600/532 |
| 5,042,501 A | 8/1991 | Kenny et al. ............... 600/532 |
| 5,060,506 A | 10/1991 | Douglas ...................... 73/24.1 |
| 5,060,655 A | 10/1991 | Rudolph ..................... 128/716 |
| 5,060,656 A | 10/1991 | Howard ...................... 128/718 |
| 5,069,220 A | 12/1991 | Casparie et al. ............ 128/719 |
| 5,072,737 A | 12/1991 | Goulding ................... 128/718 |
| 5,081,871 A | 1/1992 | Glaser ..................... 73/863.23 |
| 5,095,900 A | 3/1992 | Fertig et al. ........... 128/207.14 |
| 5,095,913 A | 3/1992 | Yelderman et al. ......... 128/719 |
| 5,117,674 A | 6/1992 | Howard ..................... 73/31.07 |
| 5,119,825 A | 6/1992 | Huhn ......................... 600/529 |
| 5,137,026 A | 8/1992 | Waterson et al. ........... 128/725 |
| 5,178,155 A | 1/1993 | Mault ......................... 128/718 |
| 5,179,958 A | 1/1993 | Mault ......................... 128/718 |
| 5,214,966 A | 6/1993 | Delsing .................. 73/861.28 |
| 5,233,996 A | 8/1993 | Coleman et al. ............ 600/529 |
| 5,282,473 A | 2/1994 | Braig et al. ................. 600/532 |
| 5,285,794 A | 2/1994 | Lynch ........................ 128/719 |
| 5,293,875 A | 3/1994 | Stone ......................... 128/719 |
| 5,299,579 A | 4/1994 | Gedeon et al. ............. 600/532 |
| 5,303,712 A | 4/1994 | Van Duren ................. 600/529 |
| 5,309,921 A | 5/1994 | Kisner et al. ............... 600/532 |
| 5,326,973 A | 7/1994 | Eckerbom et al. .......... 250/343 |
| 5,355,879 A | 10/1994 | Brain |
| 5,357,972 A | 10/1994 | Norlien ...................... 128/725 |
| 5,363,857 A | 11/1994 | Howard ...................... 600/531 |
| 5,398,695 A | 3/1995 | Anderson et al. ........... 600/532 |
| 5,402,796 A | 4/1995 | Packer et al. ................ 128/719 |
| 5,419,326 A | 5/1995 | Harnoncourt .......... 128/660.02 |
| 5,425,374 A | 6/1995 | Ueda et al. ................. 600/532 |
| 5,447,165 A | 9/1995 | Gustafsson ................. 128/719 |
| 5,450,193 A | 9/1995 | Carlsen et al. .............. 356/301 |
| 5,468,961 A | 11/1995 | Gradon et al. .............. 250/345 |
| 5,501,231 A | 3/1996 | Kaish ......................... 600/538 |
| 5,503,151 A | 4/1996 | Harnoncourt et al. ... 128/660.02 |
| 5,517,313 A | 5/1996 | Colvin, Jr. .................. 356/417 |
| 5,520,192 A | 5/1996 | Kitney et al. ............... 600/529 |
| 5,540,233 A | 7/1996 | Larsson et al. ............. 128/725 |
| 5,570,697 A | 11/1996 | Walker et al. .............. 128/719 |
| 5,590,651 A | 1/1997 | Shaffer et al. .............. 128/632 |
| 5,616,826 A | 4/1997 | Pellaux et al. ............. 73/24.02 |
| 5,632,281 A | 5/1997 | Rayburn .................... 128/719 |
| 5,645,071 A | 7/1997 | Harnoncourt et al. ....... 128/719 |
| 5,647,370 A | 7/1997 | Harnoncourt ............... 128/725 |
| 5,676,132 A | 10/1997 | Tillotson et al. ........ 128/204.23 |
| 5,705,735 A | 1/1998 | Acorn et al. ................. 73/23.3 |
| 5,740,801 A | 4/1998 | Branson ..................... 600/407 |
| 5,754,288 A | 5/1998 | Yamamoto et al. ......... 356/301 |
| 5,789,660 A | 8/1998 | Kofoed et al. ............... 73/23.3 |
| 5,795,787 A | 8/1998 | Silkoff et al. ............... 436/116 |
| 5,796,009 A | 8/1998 | Delsing ................... 73/861.28 |
| 5,800,360 A | 9/1998 | Kisner et al. ............... 600/532 |
| 5,810,747 A | 9/1998 | Brudny et al. .............. 600/595 |
| 5,816,246 A | 10/1998 | Mirza ......................... 128/726 |
| 5,831,175 A | 11/1998 | Fletcher-Haynes ........ 73/861.28 |
| 5,834,626 A | 11/1998 | DeCastro et al. ............ 73/23.3 |
| 5,836,300 A | 11/1998 | Mault ......................... 600/532 |
| 5,839,433 A | 11/1998 | Higenbottam .......... 128/204.21 |
| 5,873,359 A | 2/1999 | Zapol et al. ............. 128/203.12 |
| 5,894,351 A | 4/1999 | Colvin, Jr. .................. 356/417 |
| 5,904,938 A | 5/1999 | Zapol et al. ................. 424/718 |
| 5,910,661 A | 6/1999 | Colvin, Jr. .................. 250/573 |
| 5,917,605 A | 6/1999 | Colvin, Jr. .................. 356/417 |
| 5,922,610 A | 7/1999 | Alving et al. ............... 436/116 |
| 5,932,812 A | 8/1999 | Delsing ................... 73/861.02 |
| 5,957,128 A | 9/1999 | Hecker et al. .......... 128/204.22 |
| 5,957,858 A | 9/1999 | Micheels et al. ........... 600/532 |
| 6,010,459 A | 1/2000 | Silkoff et al. ............... 600/532 |
| 6,033,368 A | 3/2000 | Gaston, IV et al. ......... 600/532 |
| 6,038,913 A | 3/2000 | Gustafsson et al. .......... 73/23.3 |
| 6,044,843 A | 4/2000 | O'Neil et al. ........... 128/204.23 |
| 6,062,064 A | 5/2000 | Yoshida et al. .............. 73/23.2 |
| 6,063,027 A | 5/2000 | Alving et al. ............... 600/300 |
| 6,063,407 A | 5/2000 | Zapol et al. ................. 424/718 |
| 6,067,983 A | 5/2000 | Stenzler ................. 128/204.23 |
| 6,082,176 A | 7/2000 | Kondo et al. ............... 73/23.31 |
| 6,082,177 A | 7/2000 | Niazy et al. ................ 73/23.31 |
| 6,117,872 A | 9/2000 | Maxwell et al. ............ 514/249 |
| 6,190,326 B1 | 2/2001 | McKinnon et al. ......... 600/529 |

INDIRECT CALORIMETRY SYSTEM

Related Application

This application claims priority of U.S. Provisional Patent Application No. 60/236,829 filed Sep. 29, 2000, and is incorporated herein by reference.

FIELD OF THE INVENTION

This invention relates to medical equipment, in particular for the diagnosis of respiratory problems.

BACKGROUND OF THE INVENTION

Asthma and respiratory diseases are becoming widespread health problems. Various causes have been speculated, such as indoor and outdoor air pollution. Diesel-powered vehicles are known to produce particulates harmful to the lungs. Modern houses are usually well sealed and insulated, and in consequence may have high levels of indoor air pollution due to vapors such as formaldehyde exuding from carpets.

Asthma diagnosis is often achieved by measuring one or more respiratory parameters, for example, peak flow and forced exhaled volume in one second (FEV1). Diagnosis may be achieved using the variety of instruments known in the art. For example, peak flow is often measured using mechanical devices. However, existing devices may not provide the combination of flow profile data and breath parameters necessary for improved diagnosis. The volume and flow rate of inhaled or exhaled breath may be monitored using a respiratory spirometer. For spirometry, it is useful to monitor the total oxygen consumption of the patient.

Respiratory analysis can be used to diagnose lung disease, lung cancer, and other airway diseases. The presence of nitric oxide in the breath of a person is often of diagnostic significance. Several volatile organic compounds have been correlated with lung cancer. Bacterial infection of the lungs may be detected using antibody response to pathogens in exhaled breath. Thus, there exists a diagnostic need for a calorimetry system capable of readily measuring respiratory characteristics and components.

Resting metabolic rate is an important factor in the calorie balance of a person. A person's total energy expenditure (TEE) is equal to the sum of resting energy expenditure (REE) and activity-related energy expenditure (AEE), i.e.:

$$TEE = REE + AEE$$

The calorie balance for a person is the difference between the total energy expenditure and caloric intake. As part of a weight control program, a person might record caloric intake, and estimate or determine activity levels using accelerometers, pedometers, and the like. However, unless the person has accurate knowledge of REE, weight loss predictions are not possible. REE is a larger component of TEE than AEE, so that an accurate knowledge of REE is essential in calculating calorie balance. One problem in a weight control program is that REE usually falls during a diet, due to the body's natural response to perceived starvation. Hence, even significantly reducing calorie intake may not be enough to lose weight.

Obesity is a huge problem, particularly in the developed world. Many medical problems are correlated with obesity, e.g. heart problems, joint problems, etc. Hence, it is useful to a physician to assist a patient with a weight control program using an indirect calorimeter to determine metabolic rate. The current medical system often does not emphasize disease prevention; however, this may change in the near future. A physician may therefore wish to play a greater role in disease prevention, in which case professional assistance with weight control becomes important.

There are formulas in the literature (e.g. the Harris-Benedict equation) which allow calculation of metabolic rate from height and weight. If metabolic rate is significantly higher or lower than a normal range, based on such a formula, this can be diagnostic of a range of metabolism-based problems. Hence, there exists a need for a physician to measure metabolic rate of a person, as part of a diagnostic test for medical problems.

SUMMARY OF THE INVENTION

An indirect calorimetry system includes a plurality of transducers sensitive to expired airflow from a subject's lungs. A calorimetry housing encloses the plurality of transducers. The transducers' output is communicated to a microprocessor that calculates expiration characteristics and conveys those characteristics to a graphical display. In another embodiment, an indirect calorimetry system includes a plurality of transducers sensitive to expired airflow and a housing enclosing the transducers. A microprocessor in communication with the transducers calculates expiration characteristics and those characteristics are communicated by way of a communication link to devices such as a computer, a communication network such as the Internet or to a PDA.

A process for monitoring physiological gas exchange associated with respiration includes the active expiring into an indirect calorimeter for a period of time and then measuring the expiration flow with a plurality of transducers. The measurement of expiration flow is then time stamped and displayed as a function of the period of time.

DETAILED DESCRIPTION OF THE INVENTION

The present invention has utility in medical monitoring. Through monitoring of physiological gas exchange associated with respiration, the present invention affords information and/or feedback control useful in situations illustratively including pulmonary disease and condition diagnosis, weight loss and life support.

Figure 1:
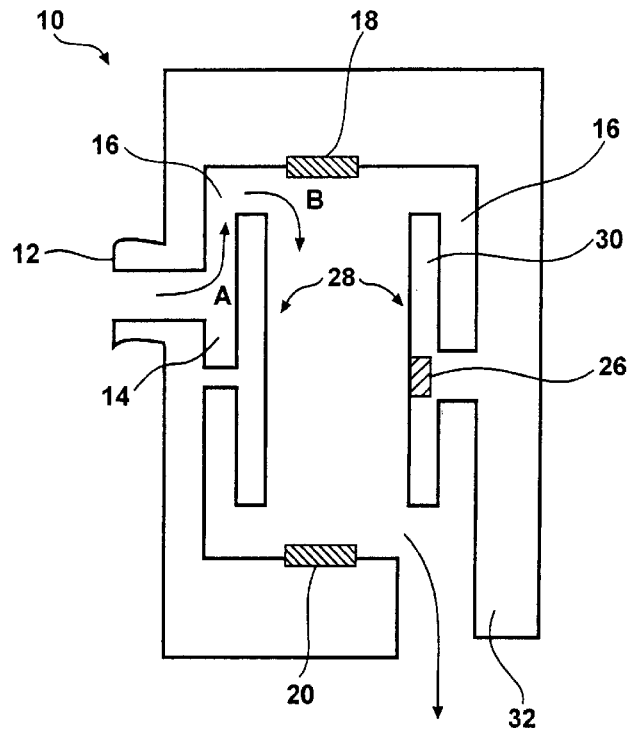
FIG. 1 is a cross-sectional view of an indirect calorimeter operative as a component of the present invention.

FIG. 1 illustrates part of a handheld indirect calorimeter described in PCT Application PCT/US99/02448. The indirect calorimeter, shown generally at 10, has a mouthpiece 12, and corresponding air vent 32 to a source/sink of respiratory gases, such as the atmosphere. Exhaled air passes through mouthpiece 12, along path A and into concentric chamber 16. Concentric chamber 16 forms a coaxial chamber around flow tube 30, and a lower region such as 14 may be used as a spit trap. This arrangement will be referred to as a coaxial flow path. Respired air passes along paths such as B into the flow column 28, formed largely by flow tube 30. Exhaled air then passes into the source/sink of respiratory gases through air vent 32. Inhaled air passes through the device in the reverse direction, entering through air vent 32. A pair of ultrasonic transducers 18 and 20 are used to determine flow direction and volume, as described in a co-pending utility application claiming priority of U.S. Provisional Patent Application No. 60/228,388. Preferably, the flow path is through a disposable portion of the indirect calorimeter. It is appreciated other devices conventional to the art are operative herein to monitor the composition of expired air. Additionally, disposable portions of a device for receiving expired air are appreciated to optionally provide an added level of device hygiene as detailed in U.S. Provisional Patent Application No. 60/179,906.

The transit time of ultrasonic pulses between the two ultrasonic transducers 18 and 20 is determined at intervals. The difference in transit times is related to the flow rate through the indirect calorimeter with flow rate determined throughout a breath. While the flow rates are optionally integrated to yield flow volume, for pulmonary diagnosis, it is often useful to obtain a flow curve of flow rate as a function of time over a breath. The system of the present invention through variable data processing and display formats is operative in a variety of medical settings.

Figure 2:
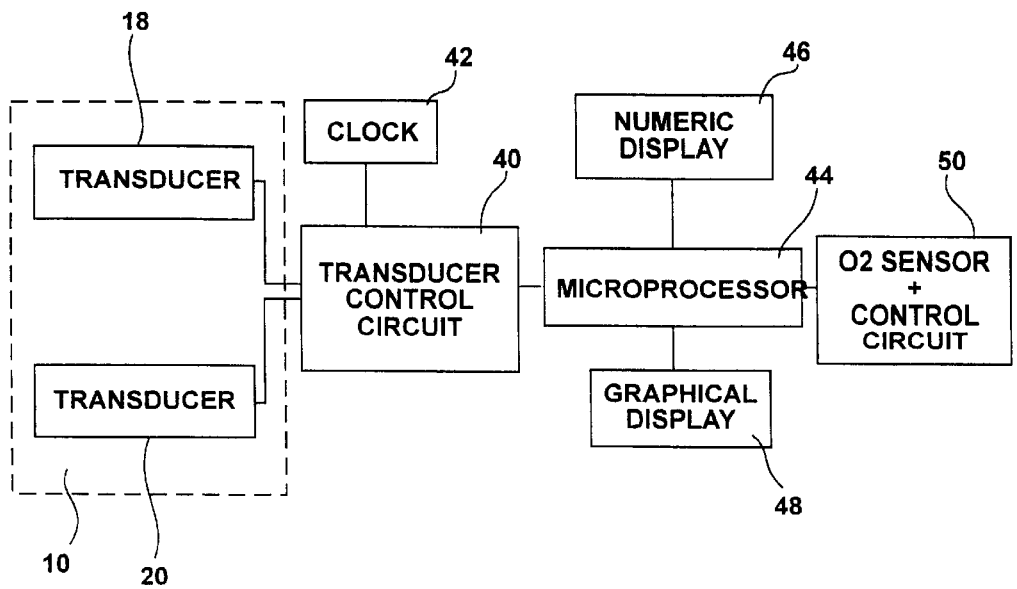
FIG. 2 is a schematic block diagram of an embodiment of the present invention adapted for display of a breath flow profile.

An indirect calorimeter is optionally equipped with a display for illustrating the flow profile of a breath. FIG. 2 is a schematic of an indirect calorimeter system adapted to display a breath flow profile. Ultrasonic control circuitry 40 is used to control the two ultrasonic transducers 18 and 20 of an indirect calorimeter 10. Flow rates are determined from the difference between the transit times for an ultrasonic pulse to be transmitted from transducer 18 and detected by transducer 20, and the transit time in the reverse direction. Transit times are optionally determined in multiples of a period of a clock 42. A microprocessor 44 receives flow value data from control circuit 40 over the period of breaths. The beginning and end of a breath is found by changes in flow direction, or periods of low flow level. The flow profile over the breath is determined by the microprocessor, and displayed on a graphical display 48. Oxygen partial pressure values from an oxygen ($O_2$) sensor also optionally are determined and used together with integrated flow date to determine oxygen consumption. The metabolic rate determined from the oxygen consumption data preferably is presented on a numeric display 46.

In operation, the flow profile for a subject is measured over a number of breaths, with the device averaging a number of satisfactory breaths. A satisfactory breath is one which meets certain parameter conditions, illustratively including well-defined start, total length, total volume, and lack of periods of reverse flow. Either from a single breath, or an average of several breaths, the device calculates respiratory parameters as described herein. It is appreciated that a subject includes not only a human, but also other air breathing creatures including pets and livestock.

Figure 3:
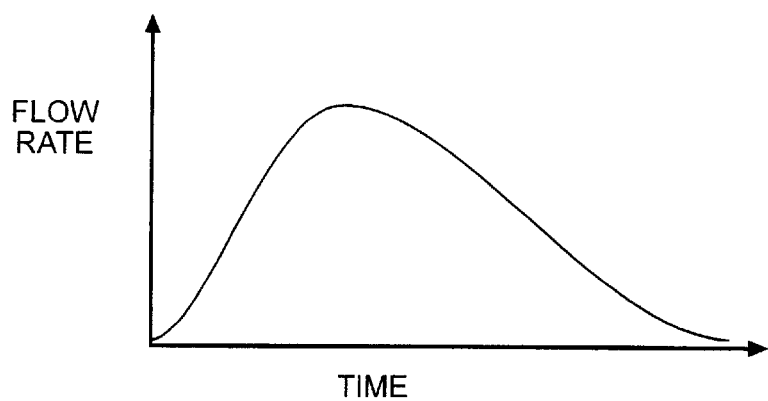
FIG. 3 is a graph illustrating an exemplary breath flow profile as a function of time.

FIG. 3 illustrates a possible breath flow profile. Such a flow profile may be compared with standard flow profiles stored in memory. The present invention may contain circuitry or software for analyzing a collected flow profile, or diagnosing problems such as airway blockage. A flow profile may be stored in a memory or database, optionally along with a time stamp. The breath parameters history may be plotted over time for a subject.

The present invention optionally has a log-in procedure for different subjects, so that collected data is uniquely identified with a given subject. Data generated by the present invention is preferably stored on a memory medium such as a memory card, which then can be reviewed by a physician or technician or transferred to a computer, PDA, or other suitable electronic device.

The memory medium, or its contents, can be added to the subject's medical log. A healthcare provider may dictate notes regarding tests stored with respiratory data, and the present invention may prompt for other patient data to be entered to accompany the stored respiratory data. The additional data may include subject identity, symptoms and the like.

A nitric oxide detector optionally is combined with the instant invention. The flow rate is monitored as a function of time, and the data transferred to a PDA via a wireless transfer (e.g. Bluetooth), IR, cables, or transfer of a memory medium. The flow rate for a single breath, or a number of averaged breaths, may then be plotted and analyzed on the PDA. Alternatively, the instant invention may be provided with a display for respiratory flow/volume graphing versus time, and with data analysis functionality, such as preloaded software, for determining parameters such as peak flow from the collected data.

The peak flow rate, the forced vital capacity (FVC), and the forced expiratory volume in the first second interval (FEV1) may be derived from the collected data, along with other parameters known in the art. The flow profile, also known as the time-dependent flow rate over the course of an exhalation or inhalation, may be combined with these parameters. The data may be transferred from the indirect calorimeter, PDA, or a combined device comprising the functionality of both, to a remote computer system using a communications network connection such as a wireless Internet connection. A health professional may view the collected data by methods such as an Internet connection, and thereby provide a guide, for instance in terms of administration of medication or behavior modification. This scheme is useful for diagnosing asthma, chronic obstructive pulmonary diseases, allergies, cancers and the like.

The instant invention also is operative as an incentive spirometer. An indirect calorimeter, or a device in communication with it, may provide audio, visual, or tactile feedback to encourage greater oxygen consumption, more regular breathing, longer breaths, or other desirable respiratory parameters. Through behavior modification, the need for pharmaceutical or invasive intervention may be lessened.

Figure 4:
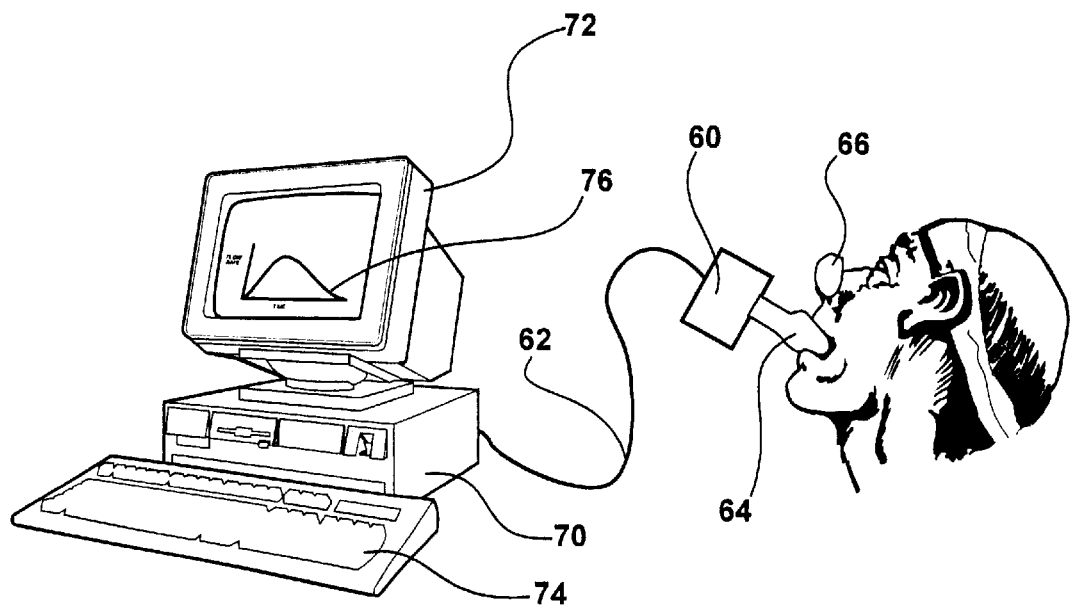
FIG. 4 is a schematic of an alternative embodiment of the present invention including a computer.

FIG. 4 shows an indirect calorimeter system including a calorimeter 60 in communication with a desktop PC 70 having a display 72 and keyboard 74. In use, a person may log onto the computer using keyboard 74, pick up the calorimeter 60 attached by a cable 62 to the computer 70, and breathe therethrough. Optionally, a mouthpiece 64 and nose clip 66 are used, alternatively a mask may be connected to the calorimeter 60. Preferably, a disposable mask or mouthpiece are used. Data is transferred to the computer 70. The display 72 may be used to show breath profiles (such as 76), metabolic rate and relaxation status. For resting metabolic rate determination, it is necessary that the person is relaxed while breathing through the calorimeter 60. Biofeedback mechanisms may be provided to show the successful achievement of a relaxed state, perhaps using a predictive algorithm to predict which relation has occurred. A subject's metabolism over time is thus monitored, and any decreases in metabolism could be compensated for by additional exercise. The measured resting metabolism may be compared with the Harris-Benedict equation. Strong deviations from the expected value may be diagnostic of metabolic disorders. The computer 70 may be connected to a communications network (not shown) allowing the user of the system and other authorized persons to access data files.

In addition to logging onto the system of FIG. 4 using the keyboard, a user alternatively may carry a key ring like device which transmits identification to the system. An interface module may be used between the calorimeter 60 and the PC 70 which contains data analysis and transmission circuitry.

A calorimeter as described herein optionally is formed of two parts, a disposable part and non-disposable part. Preferably, the flow path of respired gases from a person passes entirely through the disposable part. A unique identifying mechanism can be used so that only authorized disposable parts may be used in the calorimeter. Alternatively, the person may be requested to provide their own disposable part which they would then be supplied with either through a subscription process or through direct sale.

In the specification, the term "data transfer" refers to transfer of data from one device system, communication network, memory location, etc. to another device, network, etc. This may use any convenient method, e.g. transfer of a memory medium, e.g., a memory card or disk, a cable connection, IR, optical, wireless (such as the Bluetooth protocol) or other electrical or electromagnetic methods.

Figure 5:
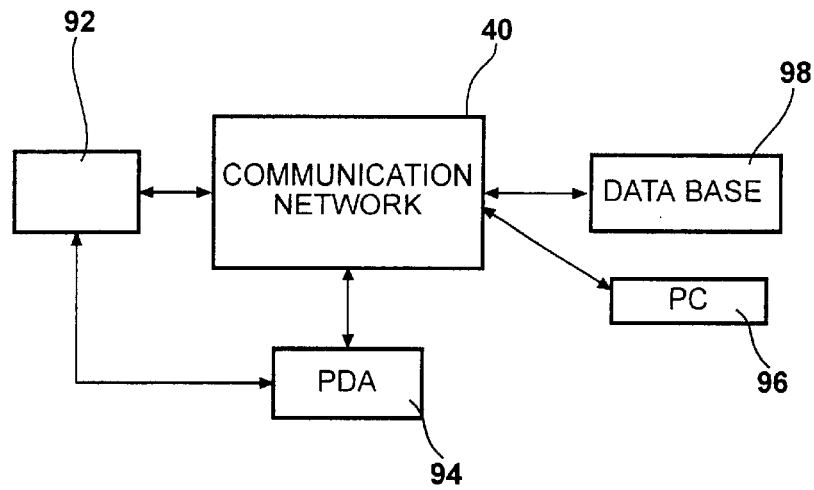
FIG. 5 is a schematic block diagram of another alternative embodiment of the present invention including a PDA interface.

FIG. 5 shows an embodiment with a calorimeter 92 in communication with PDA 94. The PDA optionally is linked to a communications network 90. PC 96 may also be in communication with the network 90. Data collected using the calorimeter 92 and PDA 94 may be stored in database 98. Alternatively, a healthcare professional may use a PDA to record medical notes on a subject, in addition to data received from the calorimeter 92.

The present invention in another embodiment is used with a patient ventilator system. The oxygen consumption as measured by the calorimeter is used to determine the feeding requirements of the person.

Figure 6:
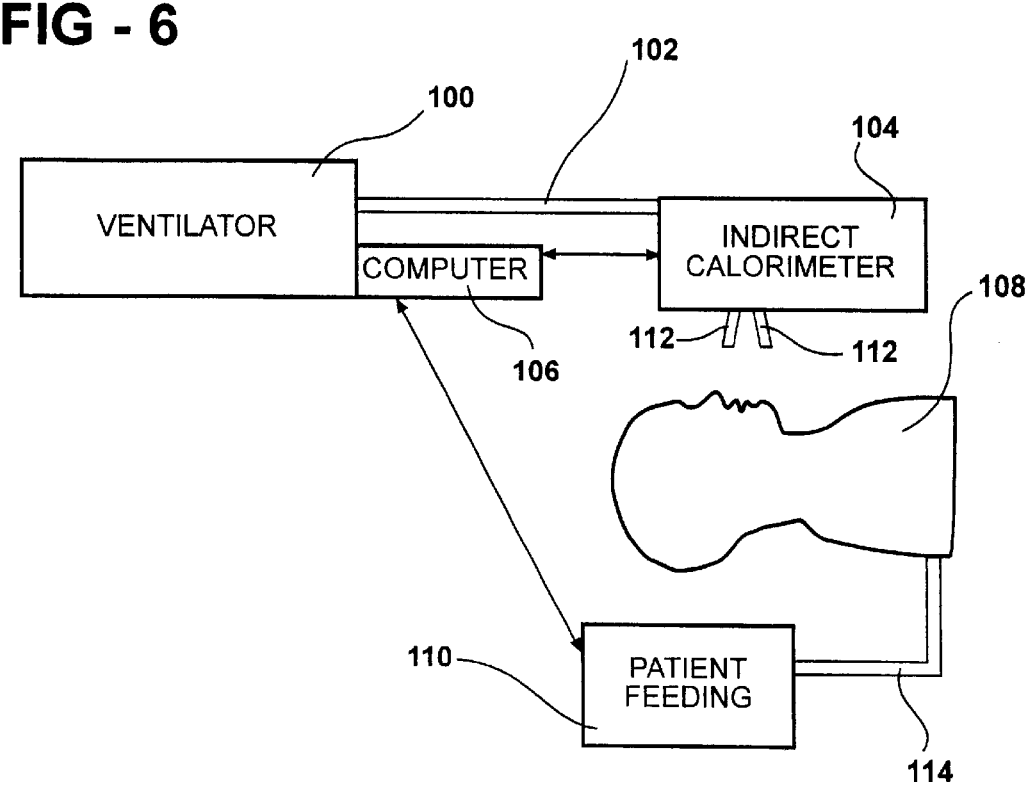
FIG. 6 is a schematic of still another alternative embodiment of the present invention including a feeding device.

FIG. 6 shows a patient 108 connected to ventilator 100 using tubing connection 102, indirect calorimeter 104, and mask 112. Preferably, the mask or mask/indirect calorimeter combination is disposable. The double-headed arrow between the calorimeter 104 flow module housing and circuitry 106 is preferably a cable, but a wireless communication method may also be used. The indirect calorimeter flow module 104 contains flow sensor(s) and optionally a gas component sensor. The oxygen consumption of the patient 108 is calculated from data obtained by the sensors in 104 and analyzed by the circuitry 106, and used to control an intravenous pumping device 110. This may operate using a feeding tube 114 connected to an intravenous feeding needle arrangement (not shown). Nutrients or medications are metered to a subject depending on the measured metabolic rate.

The patents and publications cited herein are incorporated by reference to the same extent as if each patent or publication was individually and specifically incorporated by reference.

One skilled in the art to which the invention pertains will recognize variations and modifications to the invention upon reading the specification. These variations and modifications that retain the inventive concept are intended to be within the scope of the appended claims that define the bounds of the invention.

What is claimed is:

1. An indirect calorimetry system comprising:

a plurality of transducers sensitive to expired airflow;

a calorimeter housing enclosing the plurality of transducers;

a microprocessor in communication with the plurality of transducers for calculating expiration characteristics;

an intravenous pumping device under feedback based upon the expiration characteristics; and a graphical display displaying the expiration characteristics.

2. The system of claim 1 wherein said microprocessor and said graphical display are attached to said calorimeter housing and said housing is handheld.

3. The system of claim 1 wherein said microprocessor is within a personal computer.

4. The system of claim 3 wherein said computer comprises software requiring log in prior to calculating expiration characteristics.

5. The system of claim 1 further comprising an oxygen sensor enclosed within said calorimeter housing.

6. The system of claim 1 further comprising a time-stamp circuit in communication with said microprocessor.

7. The system of claim 1 further comprising a nitric oxide sensor enclosed within said calorimeter housing.

8. The system of claim 1 further comprising a carbon dioxide sensor enclosed within said calorimeter housing.

9. The system of claim 1 further comprising a ventilator under feedback control based upon the expiration characteristics.

10. The indirect calorimeter system of claim 1 further comprising a graphical display displaying the expiration characteristics.

11. The system of claim 1 further comprising a disposable mask intermediate between a subject and the plurality of transducers.

12. The system of claim 1, wherein said microprocessor is operative to calculate expiration characteristics selected from the group consisting of: flow rate, flow profile, and flow volume.

13. The system of claim 12, wherein said microprocessor is further operative to process data corresponding to said calculated expiration characteristics, and determine therefrom one or more respiratory characteristics of a user, said respiratory characteristics selected from the group consisting of: peak flow rate, forced vital capacity (FVC), and forced exhaled volume in one second (FEV1).

14. The system of claim 1, further including a signaling device which is in communication with said microprocessor, said signaling device being operative to provide an audible, visual or tactile feedback signal to a user, said feedback signal corresponding to an expiration characteristic calculated by said microprocessor.

15. The system of claim 14, wherein said feedback signal is provided in real time.

16. The system of claim 1, wherein said calorimeter housing includes a mouthpiece configured for a user to breathe into and out of a vent to a source/sink; of respiratory gases and a chamber in fluid communication with said mouthpiece and source/sink; said housing further including a flow tube disposed in said chamber, in a concentric relationship therewith, said flow tube being disposed so that at least a portion of a gas passing between the mouthpiece and the source/sink will pass through said flow tube.

17. An indirect calorimetry system comprising:
- a plurality of transducers sensitive to expired airflow;
- a calorimeter housing enclosing the plurality of transducers;
- a microprocessor in communication with the plurality of transducers for calculating expiration characteristics;
- a communications link to a device selected from the group consisting of: a computer, a communication network, and a PDA; and
- an intravenous pumping device under feedback control based upon the expiration characteristics.

18. The system of claim 17 further comprising a nitric oxide sensor enclosed within said calorimeter housing.

19. The system of claim 17 further comprising a carbon dioxide sensor enclosed within said calorimeter housing.

20. The system of claim 17 further comprising a ventilator under feedback control based upon the expiration characteristics.

21. The system of claim 17, wherein said calorimeter housing includes a mouthpiece configured for a user to breathe into and out of a vent to a source/sink; of respiratory gases and a chamber in fluid communication with said mouthpiece and source/sink; said housing further including a flow tube disposed in said chamber, in a concentric relationship therewith, said flow tube being disposed so that at least a portion of a gas passing between the mouthpiece and the source/sink will pass through said flow tube.

22. The system of claim 17 further comprising a disposable mask intermediate between a subject and the plurality of transducers.

23. The system of claim 17 wherein said microprocessor and a graphical display are attached to said calorimeter housing and said housing is handheld.

24. The system of claim 17 wherein said microprocessor is within a personal computer.

25. The system of claim 24 wherein said computer comprises software requiring log in prior to calculating expiration characteristics.

26. The system of claim 17 further comprising an oxygen sensor enclosed within said calorimeter housing.

27. The system of claim 17 further comprising a time-stamp circuit in communication with said microprocessor.

28. An indirect calorimetry system comprising:
- a plurality of transducers sensitive to expired airflow;
- a housing enclosing the plurality of transducers;
- a microprocessor in communication with the plurality of transducers for calculating expiration characteristics; and
- an intravenous pumping device under feedback control based upon the calculated expiration characteristics.

29. An indirect calorimetry system comprising:
- a plurality of transducers sensitive to expired airflow;
- a housing enclosing the plurality of transducers;
- a microprocessor in communication with the plurality of transducers for calculating expiration characteristics;
- a communications link to a device selected from the group consisting of: a computer, a communication network, and a PDA; and
- an intravenous pumping device under feedback control based upon the expiration characteristics.

30. A method for monitoring a respiratory characteristic of a patient, said method comprising the steps of:
- providing a monitoring system comprising:
  - a source/sync of respiratory gasses;
  - a mouthpiece;
  - a chamber in fluid communication with said mouthpiece and said source/sync;
  - a flow path in communication with said mouthpiece;
  - a flow tube disposed in said chamber, in concentric relationship therewith, said flow tube being disposed so that at least a portion of said flow path will pass through said flow tube;
  - a plurality of ultrasonic transducers disposed in said flow path, said transducers being operable to generate a signal corresponding to a flow of a gas through said flow path; and a microprocessor in communication with said plurality of transducers, said microprocessor being operable to receive said signal and calculate one or more of: flow rate, flow profile and flow volume, of a gas passing through said flow path;
- directing a patient to breathe through said mouthpiece so as to generate a flow of gas therethrough;
- operating the microprocessor so as to calculate said characteristic of the flow of gas initiated by said patient; and
- determining a respiratory characteristic of said patient from said at least one expiration characteristic, said respiratory characteristic being selected from the group consisting of: peak flow rate, forced vital capacity (FVC), and forced exhaled volume in one second (FEV1).

* * * * *